(12) United States Patent
Chen et al.

(10) Patent No.: US 8,110,380 B2
(45) Date of Patent: Feb. 7, 2012

(54) STARCH-BASED BIODEGRADABLE MATERIAL COMPOSITION

(75) Inventors: C. Will Chen, Taipei (TW);
Ching-Huang Wang, Taipei (TW);
Chin-Wei Chen, Hsinchu (TW);
Yun-Ping Wang, Taichung (TW)

(73) Assignee: Grace Biotech Corporation, Hsinchu County (TW)

( * ) Notice: Subject to any disclaimer, the term of this patent is extended or adjusted under 35 U.S.C. 154(b) by 529 days.

(21) Appl. No.: 12/149,201

(22) Filed: Apr. 29, 2008

(65) Prior Publication Data

US 2009/0075346 A1    Mar. 19, 2009

(30) Foreign Application Priority Data

Sep. 18, 2007    (TW) ............................... 96134826 A

(51) Int. Cl.
*C12P 19/14*    (2006.01)
*C07H 1/00*    (2006.01)

(52) U.S. Cl. ............. 435/99; 435/95; 435/98; 435/201; 435/202; 435/203; 435/205; 435/211; 536/4.1; 536/18.5; 536/123.1; 536/123.13; 536/124; 536/128; 536/1.11

(58) Field of Classification Search .................. 435/95, 435/96, 98, 99, 201, 202, 203, 205, 210, 435/211; 536/1.11, 4.1, 18.5, 123.1, 123.13, 536/124, 128
See application file for complete search history.

(56) References Cited

U.S. PATENT DOCUMENTS

| 5,445,678 | A | * | 8/1995 | Whistler | ......................... 127/67 |
| 5,576,049 | A | * | 11/1996 | Haas et al. | ................. 427/389.9 |
| 5,703,160 | A | | 12/1997 | Dehennau et al. | |
| 6,184,261 | B1 | | 2/2001 | Biby et al. | |
| 2002/0184662 | A1 | * | 12/2002 | Henson et al. | ................. 800/284 |
| 2005/0137303 | A1 | * | 6/2005 | Shelby et al. | ................. 524/284 |

FOREIGN PATENT DOCUMENTS

| CN | 1948374 A | 4/2007 |
| CN | 1313016 C | 5/2007 |
| JP | 2001316495 | 11/2010 |
| TW | 552290 B | 9/2003 |
| WO | WO 2005097875 A1 * | 10/2005 |
| WO | WO 2008/072114 A | 6/2008 |

OTHER PUBLICATIONS

STN Registry printout for Ecruamide (Registry No. 112-84-5); downloaded Dec. 2, 2010.*
STN Restiry printout for polymer of 1,4-benzenedicarboxylic acid, 1,4-butanediol and hexanedoic acid, Registry No. 60961-73-1; downloaded Nov. 28, 2010.*
English machine trasnlation of JP 2001-316495 downloaded from the JPO on Nov. 28, 2011.*
Mu et al. (2008) Chemical Physics 348: 122-129.*
Database CA Chemical Abstracts Service, Columbus, Ohio; Watanabe et al, "Aliphatic polyester-based biodegradable films for raw trash treating system", XP002506547 retrieved from STN Database accession No. 2001:823408 *abstract*.

* cited by examiner

*Primary Examiner* — Susan Hanley
(74) *Attorney, Agent, or Firm* — Nixon & Vanderhye P.C.

(57) ABSTRACT

A starch-based biodegradable material composition includes: an enzyme-hydrolyzed starch; and a biodegradable polyester selected from at least one of an aliphatic polyester of polybutylene succinate and an aliphatic-aromatic copolyester. The enzyme-hydrolyzed starch is prepared by hydrolyzing a native starch using a starch-hydrolyzing enzyme. The starch-hydrolyzing enzyme has an activity unit ranging from 15000 to 40000.

20 Claims, No Drawings

STARCH-BASED BIODEGRADABLE MATERIAL COMPOSITION

CROSS-REFERENCE TO RELATED APPLICATION

This application claims priority of Taiwanese application no. 096134826, filed on Sep. 18, 2007.

BACKGROUND OF THE INVENTION

1. Field of the Invention

This invention relates to a starch-based biodegradable material composition, more particularly to a starch-based biodegradable material composition including a biodegradable polyester selected from at least one of an aliphatic polyester of polybutylene succinate and an aliphatic-aromatic copolyester 2. Description of the Related Art A conventional biodegradable material composition usually includes a native starch blended with a polymer so as to enhance the mechanical strength of the biodegradable material composition. However, the native starch has two large molecular groups of amylose and amylopectin, which can result in poor blending with the polymer due to stereo-hindrance of the molecular structure of the native starch.

It is known in the art to use a chemically modified starch to enhance the blending efficiency. However, chemical modification of the native starch is relatively complex and has drawbacks, such as undesired chemical residue and low microorganism degradable rate.

Taiwanese patent no. 552290 discloses a biodegradable material composition including an enzyme-hydrolyzed starch, which is prepared by hydrolyzing a native starch using a starch-hydrolyzing enzyme, a polyvinyl alcohol, a plasticizer, and a property-improving agent. Although the biodegradable material composition has excellent biodegradability, films made therefrom have a relatively poor tensile strength and can only be used for production of foam materials or plate materials.

SUMMARY OF THE INVENTION

Therefore, an object of the present invention is to provide a starch-based biodegradable material composition that can overcome the aforesaid drawback associated with the prior art.

Another object of this invention is to provide a method for making a starch-based biodegradable material composition.

According to one aspect of the present invention, a starch-based biodegradable material composition comprises: an enzyme-hydrolyzed starch; and a biodegradable polyester selected from at least one of an aliphatic polyester of polybutylene succinate and an aliphatic-aromatic copolyester.

According to another aspect of this invention, there is provided a method for making a starch-based biodegradable material composition that comprises: (a) mixing a native starch with a biodegradable polyester so as to form a solid mixture; (b) mixing a starch-hydrolyzing enzyme with a liquid additive so as to form a liquid mixture; and (c) blending the solid mixture and the liquid mixture so as to induce hydrolyzation of the native starch and chemical blending of the hydrolyzed starch and the biodegradable polyester to form the starch-based biodegradable material composition.

DETAILED DESCRIPTION OF THE PREFERRED EMBODIMENTS

The preferred embodiment of a starch-based biodegradable material composition of this invention includes: an enzyme-hydrolyzed starch; and a biodegradable polyester selected from at least one of an aliphatic polyester of polybutylene succinate (PBS) and an aliphatic-aromatic copolyester.

In order to enhance properties of the starch-based biodegradable material composition, such as mechanical strength, anti-oxidation, stability, and anti-hardness, the starch-based biodegradable material composition preferably is compounded with additives such as a plasticizer and a strength-improving agent.

In the preferred embodiment, the starch-based biodegradable material composition further includes a plasticizer made from a material selected from the group consisting of glycerol, lecithin, polyethylene glycol, ethylene glycol, propylene glycol, sorbitol, and combinations thereof. More preferably, the plasticizer is selected from the group consisting of glycerol, lecithin, and combinations thereof.

In one preferred embodiment of the invention, the aliphatic-aromatic copolyester is polybutylene adipate/terephthalate (PBAT).

In the preferred embodiment, the starch-based biodegradable material composition further includes a strength-improving agent selected from the group consisting of $TiO_2$, CaO, $CaCO_3$, silica, and combinations thereof.

Preferably, the enzyme-hydrolyzed starch has a weight ratio to the biodegradable polyester ranging from 0.6 to 2.6, and more preferably, from 1.1 to 2.6.

Preferably, the enzyme-hydrolyzed starch has a weight ratio to the plasticizer ranging from 0.014 to 0.4, and more preferably, from 0.17 to 0.36.

In the preferred embodiment, the enzyme-hydrolyzed starch is prepared by hydrolyzing a native starch using a starch-hydrolyzing enzyme.

It is noted that the activity unit (U) of the starch-hydrolyzing enzyme is a measure of the rate of conversion of the native starch into a reducing sugar end per minute per gram of the starch-hydrolyzing enzyme.

Preferably, the starch-hydrolyzing enzyme has an activity unit ranging from 15000 to 40000 U.

Preferably, the native starch has a weight ratio to the starch-hydrolyzing enzyme not greater than 190, and more preferably, not greater than 100.

Preferably, the native starch is selected from the group consisting of tapioca starch, potato starch, gramineae starch, corn starch, wheat starch, legume starch, and combinations thereof. More preferably, the native starch is selected from the group consisting of tapioca starch, corn starch, wheat starch and combinations thereof.

Preferably, the starch-hydrolyzing enzyme is selected from the group consisting of α-amylase, β-amylase, isoamylase, glucoamylase, pullulanase, cyclodextrin glucano-transferase (CGTase), β-fructofuranosidase, glucose isomerase, and combinations thereof. In the preferred embodiment, the starch-hydrolyzing enzyme is α-amylase.

This invention also provides a method for making the starch-based biodegradable material composition, including: (a) mixing the native starch with a biodegradable polyester so as to form a solid mixture; (b) mixing the starch-hydrolyzing enzyme with a liquid additive so as to form a liquid mixture; and (c) blending the solid mixture and the liquid mixture so as to induce hydrolyzation of the native starch and chemical blending of the hydrolyzed starch and the biodegradable polyester to form the starch-based biodegradable material composition.

Preferably, the starch-hydrolyzing enzyme remains active within in a temperature ranging from 25° C. to 110° C., more preferably, from 55° C. to 110° C., and most preferably, from 75° C. to 105° C.

Preferably, the liquid additive is selected from water, a plasticizer and combinations thereof.

Preferably, the liquid additive contains water and the plasticizer at a weight ratio ranging from 1:1 to 1:3.

Optionally, a strength-improving agent can be added into the solid mixture. Preferably, addition of the strength-improving agent is conducted prior to step (a).

Preferably, the native starch, the biodegradable polyester and the liquid additive have a weight ratio ranging from 1:0.6:0.3 to 1:2.6:0.5, and more preferably, from 1:1.1:0.3 to 1:2.6:0.5.

This invention further provides a starch-based biodegradable film made from the starch-based biodegradable material composition.

The starch-based biodegradable film thus formed can be used for making a lightweight raincoat, a shopping bag, a garbage bag, or an agriculture mulch, and decomposes into carbon dioxide and water after a period of use.

This invention additionally provides a method of making the starch-based biodegradable film. The method includes: (a) mixing the native starch with the biodegradable polyester so as to form a solid mixture: (b) mixing the starch-hydrolyzing enzyme with the liquid additive so as to form a liquid mixture; and (c) extruding the solid mixture and the liquid mixture so as to induce hydrolyzation of the native starch and chemical blending of the hydrolyzed starch and the biodegradable polyester to form the starch-based biodegradable material film.

In the embodiment, the extruding in step (c) is conducted through twin screw extruder techniques.

The merits of the biodegradable material composition of this invention will become apparent with reference to the following Examples and Comparative Examples.

EXAMPLES

Table 1 shows the content of each of the components of the starch-based biodegradable material composition of Examples 1-16 and Comparative Examples 1 and 2.

Examples 1-7

E1-E7

A total amount of 100 kg resin containing tapioca starch, polybutylene adipate/terephthalate (PBAT, BASF CO. Ecoflex), glycerol, water, lecithin and a starch-hydrolyzing enzyme was prepared in each of the Examples. First, the tapioca starch was put into a container, and the PBAT was then added thereto. The glycerol, water, lecithin and the starch-hydrolyzing enzyme were mixed and were added into the container. The mixture thus formed was extruded using a Twin Screw Extruder (Coperion-Werner & Pfleiderer Co. ZSK92) so as to form a resin pellet of the starch-based biodegradable material composition. The extruding conditions were as follows: The ratio of screw length/screw diameter was 44. The feeding rate was 280 kg/hr, and the rotational speed of the screw was about 180 rpm. The temperatures of different segments of the extrusion screw were about 30° C., 110° C., 115° C., 120° C., 125° C., 125° C., 130° C., 135° C., 135° C., 125° C., and 80° C., respectively.

Example 8

E8

The process conditions of Example 8 were similar to those of Examples 1-7, except that 0.3 wt % $TiO_2$ serving as the strength-improving agent was added into the container and mixed with the tapioca starch.

Examples 9-11

E9-E11

The process conditions of Examples 9-11 were similar to those of Examples 1-7, except that the rotational speed of the screw was 250 rpm for the extrusion, and the temperatures of the different segments of the extrusion screw were about 30°

TABLE 1

| | Starch (wt %) | | | Polyester (wt %) | | Liquid additive (wt %) | | | |
| --- | --- | --- | --- | --- | --- | --- | --- | --- | --- |
| | Tapioca starch | Wheat starch | Corn starch | PBAT | PBS | Enzyme | Glycerol | Water | Lecithin |
| E1 | 44.8 | — | — | 38.8 | — | 0.5 | 11.9 | 3.5 | 0.5 |
| E2 | 26.1 | — | — | 61 | — | 0.39 | 9 | 3.12 | 0.39 |
| E3 | 32.6 | — | — | 49 | — | 0.5 | 13.1 | 4.3 | 0.5 |
| E4 | 35 | — | — | 52 | — | 0.5 | 9 | 3 | 0.5 |
| E5 | 38.6 | — | — | 46.5 | — | 0.5 | 10.4 | 3.5 | 0.5 |
| E6 | 48 | — | — | 36 | — | 0.5 | 11.2 | 3.8 | 0.5 |
| E7 | 33 | — | — | 50 | — | 0.5 | 12 | 4 | 0.5 |
| *E8 | 34.7 | — | — | 52 | — | 0.52 | 8.8 | 3.16 | 0.52 |
| E9 | 42.1 | — | — | 42.1 | — | 0.55 | 11.2 | 3.8 | 0.25 |
| E10 | 44.9 | — | — | 38.4 | — | 0.26 | 12 | 3.94 | 0.5 |
| E11 | 35 | — | — | 52 | — | 0.5 | 6 | 6 | 0.5 |
| E12 | — | 34.9 | — | 52.5 | — | 0.5 | 8.9 | 3.2 | — |
| E13 | — | — | 35 | 52 | — | 0.5 | 6 | 6 | 0.5 |
| E14 | — | — | 35 | 52 | — | 0.5 | 12 | — | 0.5 |
| E15 | — | — | 35 | 52 | — | 0.5 | — | 12 | 0.5 |
| E16 | — | — | 35 | — | 52 | 0.5 | 9 | 3 | 0.5 |
| CE1 | — | — | 33 | poly lactic acid 50 | | 0.5 | 13 | 3 | 0.5 |
| CE2 | — | — | 35 | polycaprolactone 52 | | 0.5 | 9 | 3 | 0.5 |

*E8 further includes 0.3 wt % $TiO_2$

C., 110° C., 120° C., 125° C., 125° C., 125° C., 130° C., 135° C., 135° C., 125° C., and 90° C., respectively.

Example 12

E12

The process conditions of Example 12 were similar to those of Examples 9-11, except that the native starch was wheat starch.

Examples 13-15

E13-E15

The process conditions of Examples 13-15 were similar to those of Examples 9-11, except that the native starch was corn starch.

Example 16

E16

The process conditions of Example 16 were similar to those of Examples 9-11, except that the native starch was corn starch and the biodegradable polyester was polybutylene succinate (PBS, IRE Chemicals Co. Enpol 8086).

Comparative Example 1

CE1

The process conditions of Comparative Example 1 were similar to those of Examples 1-7, except that that the native starch was corn starch and the biodegradable polyester was poly lactic acid (PLA). The temperatures of different segments of the extrusion screw were about 30° C., 95° C., 95° C., 100° C., 160° C., 170° C., 170° C., 165° C., 150° C., 130° C., and 100° C., respectively. The feeding rate was 300 kg/hr. The compounded mixture became paste in the twin screw extruder and was unable to be formed into resin pellet for subsequent film blowing operation.

Comparative Example 2

CE2

The process conditions of Comparative Example 2 were similar to those of Examples 1-7, except that that the native starch was corn starch and the biodegradable polyester was polycaprolactone (PCL, having a melt temperature ranging from 55° C. to 65° C.). The temperatures of different segments of the extrusion screw were about 30° C., 95° C., 95° C., 100° C., 115° C., 120° C., 120° C., 110° C., 90° C., 70° C., and 50° C., respectively. The feeding rate was 300 kg/hr. The compounded mixture became paste in the twin screw extruder and was unable to be formed into resin pellet for subsequent film blowing operation.

The Blown Film Condition.

Examples 1-16

The resin pellets of each of Examples 1-16 were fed into a blown film extruder (L/D=26/1, screw diameter=45 mm, die diameter=80 mm, die space=1.3 mm, rotation rate of screw=0-130 rpm, width of air ring=200 mm) to form the starch-based biodegradable films having various thicknesses (as shown in Table 2). The film blowing conditions are as follows: the resin pellets were dried under a temperature of 80° C. for 1-4 hr. The temperatures of first, second, third fourth, and fifth barrels were 125±2° C., 130±2° C., 135±2° C., 130±2° C., and 125±2° C., respectively. The extrusion speed was 18 rpm. The extrusion current was 26 amperes. The take-up speed was 13 m/min. The blow-up ratio was 3.0. The film had a width of 380 mm.

Commercial Product (CP)

A commercial product of a plastic bag made from polyester, which is not a biodegradable material, was used as a comparison. The plastic bag had a length of 50 cm, a width of 32 cm and a gusset of 18 cm long, and a capacity of 15 liters.

Comparative Example 3

CE3

A biodegradable plastic bag, having a trade name of Mater-Bi®, and produced by Novamont Co., had a film thickness of 0.08 mm and was used as Comparative Example 3.

Test of Mechanical Properties

Mechanical properties including maximum tensile strength, elongation at break, and yield strength in the longitudinal (L) and transverse (T) directions for the biodegradable films of Examples 1-16, the plastic bag of CE3, and the non-biodegradable commercial product (CP) were tested using a tensile strength testing machine (GS-QC-Tester Instrument Enterprise Co., Ltd., GS-1560/20-0230). The test results are shown in Table 2.

TABLE 2

| | Film Thickness | Maximum Tensile Strength (Mpa) | | Elongation at break (%) | | Yield strength (Mpa) | |
|---|---|---|---|---|---|---|---|
| | (mm) | L | T | L | T | L | T |
| E1 | 0.03 | 12.4 | 8.63 | 428.78 | 426.03 | 6.9 | 3.14 |
| E2 | 0.04 | 16.08 | 10.83 | 579.48 | 862.03 | 8.63 | 7.57 |
| E3 | 0.04 | 11.34 | 9.85 | 538.65 | 691.76 | 4.47 | 5.18 |
| E4 | 0.04 | 17.78 | 8.81 | 586.69 | 692.79 | 7.61 | 3.16 |
| E5 | 0.04 | 20.69 | 10.86 | 799.02 | 665.27 | 14.98 | 4.12 |
| E6 | 0.04 | 8.5 | 6.79 | 49.62 | 172.75 | 3.4 | 3.38 |
| E7 | 0.06 | 18.28 | 15.34 | 686.18 | 877.65 | 8.43 | 8.43 |
| *E8 | 0.06 | 11.95 | 4.71 | 586.83 | 652.42 | 5.96 | 2.3 |
| E9 | 0.06 | 10.88 | 3.95 | 510.79 | 542.03 | 6.12 | 2.4 |
| E10 | 0.06 | 7.82 | 4.6 | 335.2 | 649.88 | 3.42 | 2.72 |
| E11 | 0.06 | 6.51 | 5.62 | 289.82 | 630.5 | 2.56 | 2.3 |
| E12 | 0.06 | 14.43 | 5.44 | 541.09 | 722.66 | 5.8 | 2.69 |
| E13 | 0.04 | 22.52 | 10.39 | 684.66 | 674.24 | 11.04 | 4.32 |
| E14 | 0.04 | 15.14 | 14.44 | 1018.19 | 483.02 | 10.95 | 5.45 |
| E15 | 0.06 | 8.68 | 7.74 | 312.31 | 607.44 | 3.09 | 3.87 |
| E16 | 0.03 | 17.36 | 11.4 | 392.98 | 609.04 | 5.6 | 4.29 |
| CE1 | | Fail to form a film | | | | | |
| CE2 | | Fail to form a film | | | | | |
| CP | 0.04 | 22.48 | 20.59 | 539.91 | 676 | 12.63 | 9.66 |
| CE3 | 0.08 | 19.49 | 14.54 | 274.98 | 85.09 | 14.17 | 6.72 |

*E8 further includes 0.3 wt % $TiO_2$.

From the results shown in Table 2, the maximum tensile strengths of Examples 1-16 are in a ratio to that of the commercial product (CP) ranging from 0.3 to 1, which indicates that the starch-based biodegradable films of Examples 1-16 are suitable for making film products, such as lightweight raincoats, agricultural mulch, storage bags and shopping bags.

In addition, as compared to Comparative Example 3, the starch-based biodegradable films of Examples 1-5, 13, 14, and 16 exhibit a similar or even higher mechanical strength with only one half film thickness of the film of Comparative Example 3.

Moreover, the biodegradable films formed respectively from tapioca starch (E1-11), wheat starch (E12), and corn starch (E13-16), which serve as the native starch, have similar mechanical strengths.

Furthermore, the results show that PBAT polyester (Example 4) and PBS polyester (Example 16) both exhibit a good blending ability with the enzyme-hydrolyzed starch.

Load Capacity Testing

The resin pellets of Example 14 were fed into a blown film extruder so as to form a starch-based biodegradable film with a film thickness of 0.025 mm, and the film was made into a 15 liter plastic bag having a commercial standard of 50 cm×32 cm with 18 cm gusset. 8 bottles of mineral water, each of which was 0.65 kg in weight, were put into the plastic bag. The loaded plastic bag was hung in the air for 2.5/day. The results show that no cracking was found in the starch-based biodegradable film.

Biodegradable Testing

The starch-based biodegradable film of Example 4 was analyzed based on a standard of ISO14855. The testing results show that the starch-based biodegradable film of Example 4 achieves 100% biodegradability in 89/days. In addition, the starch-based biodegradable film of Example 4 has passed EN 13432 and ASTM norm D 6400-04 tests conducted by Organic Waste System laboratory, a GLP laboratory certified by the European Union, and obtained certifications of 'OK COMPOST', 'DIN CERTCO' of the EU, 'COMPOSTABLE' of the USA, and 'GreenPla' of the Japan.

With the inclusion of at least one of the aliphatic polyester of polybutylene succinate and the aliphatic-aromatic copolyester in the starch-based biodegradable material composition of this invention, the aforesaid drawback associated with the prior art can be eliminated.

With the invention thus explained, it is apparent that various modifications and variations can be made without departing from the spirit of the present invention. It is therefore intended that the invention be limited only as recited in the appended claims.

What is claimed is:

1. A starch-based biodegradable material composition comprising:
    an enzyme-hydrolyzed starch; and a biodegradable polyester selected from at least one of polybutylene succinate and polybutylene adipate/terephthalate, wherein said starch-based biodegradable material composition is made by a method comprising the steps of:
    (a) mixing a native starch with a biodegradable polyester selected from at least one of polybutylene succinate and polybutylene adipate/terephthalate so as to form a solid mixture;
    (b) mixing a starch-hydrolyzing enzyme with a liquid additive so as to form a liquid mixture; and
    (c) blending the solid mixture and the liquid mixture so as to induce hydrolysis of the native starch to form the enzyme-hydrolyzed starch; and
    (d) chemically blending the enzyme-hydrolyzed starch and the biodegradable polymer to form the starch-based biodegradable material;
    wherein the starch-hydrolyzing enzyme has an activity ranging from 15000 U to 40000 U and wherein said native starch has a weight ratio to said starch enzyme not greater than 190.

2. The starch-based biodegradable material composition of claim 1, further comprising a plasticizer selected from the group consisting of glycerol, lecithin, and a combination thereof.

3. The starch-based biodegradable material composition of claim 2, further comprising a strength-improving agent selected from the group consisting of $TiO_2$, CaO, $CaCO_3$, silica, and combinations thereof.

4. The starch-based biodegradable material composition of claim 2, wherein said enzyme-hydrolyzed starch has a weight ratio to said biodegradable polyester ranging from 0.6 to 2.6.

5. The starch-based biodegradable material composition of claim 4, wherein said enzyme-hydrolyzed starch has a weight ratio to said biodegradable polyester ranging from 1.1 to 2.6.

6. The starch-based biodegradable material composition of claim 5, wherein said enzyme-hydrolyzed starch has a weight ratio to said plasticizer ranging from 0.014 to 0.4.

7. The starch-based biodegradable material composition of claim 6, wherein said enzyme-hydrolyzed starch has a weight ratio to said plasticizer ranging from 0.17 to 0.36.

8. The starch-based biodegradable material composition of claim 1, wherein said native starch has a weight ratio to said starch-hydrolyzing enzyme not greater than 100.

9. The starch-based biodegradable material composition of claim 8, wherein said native starch is selected from the group consisting of tapioca starch, corn starch, wheat starch, potato starch, gramineae starch, legume starch, and combinations thereof.

10. The starch-based biodegradable material composition of claim 1, wherein said starch-hydrolyzing enzyme is selected from the group consisting of $\alpha$-amylase, $\beta$-amylase, isoamylase, glucoamylase, pullulanase, cyclodextrin glucano-transferase, $\beta$-fructofuranosidase, and combinations thereof.

11. A method for making a starch-based biodegradable material composition comprising:
    (a) mixing a native starch with a biodegradable polyester selected from at least one of polybutylene adipate/terephthalate and polybutylene succinate so as to form a solid mixture;
    (b) mixing a starch-hydrolyzing enzyme with a liquid additive so as to form a liquid mixture;
    (c) blending the solid mixture and the liquid mixture so as to induce hydrolysis of the native starch to form the enzyme-hydrolyzed starch; and
    (d) chemically blending of the enzyme-hydrolyzed starch and the biodegradable polyester to form the starch-based biodegradable material composition, wherein the starch-hydrolyzing enzyme has an activity ranging from 15000 U to 40000 U and wherein said native starch has a weight ratio to said starch enzyme not greater than 190.

12. The method of claim 11, wherein the starch-hydrolyzing enzyme is active within a temperature ranging from 25° C. to 110° C.

13. The method of claim 11, wherein the liquid additive is selected from water, a plasticizer, and a combination thereof.

14. The method of claim 13, wherein the liquid additive contains water and the plasticizer at a weight ratio ranging from 1:1 to 1:3.

15. The method of claim 11, wherein the solid mixture includes a strength-improving agent selected from the group consisting of $TiO_2$, CaO, $CaCO_3$, silica, and combinations thereof.

16. The method of claim 11, wherein the native starch, the biodegradable polyester and the liquid additive have a weight ratio ranging from 1:0.6:0.3 to 1:2.6:0.5.

17. The method of claim 16, wherein the native starch, the biodegradable polyester and the liquid additive have a weight ratio ranging from 1:1.1:0.3 to 1:2.6:0.5.

18. A starch-based biodegradable film that comprises:
an enzyme-hydrolyzed starch; and a biodegradable polyester selected from at least one of polybutylene succinate and polybutylene adipate/terephthalate, wherein said starch-based biodegradable film composition is made by a method comprising the steps of:
(a) mixing a native starch with a biodegradable polyester selected from at least one of polybutylene succinate and polybutylene adipate/terephthalate so as to form a solid mixture;
(b) mixing a starch-hydrolyzing enzyme with a liquid additive so as to form a liquid mixture;
(c) mixing the solid mixture and liquid mixture together; and
(d) extruding the resultant mixture from step (c) so as to induce hydrolysis of the native starch and chemical blending of the resultant enzyme-hydrolyzed starch and the biodegradable polyester to form the starch-based biodegradable film wherein the starch-hydrolyzing enzyme has an activity ranging from 15000 U to 40000 U and wherein said native starch has a weight ratio to said starch enzyme not greater than 190.

19. A method of making a starch-based biodegradable film comprising:
(a) mixing a native starch with a biodegradable polyester selected from at least one of polybutylene succinate and polybutylene adipate/terephthalate so as to form a solid mixture;
(b) mixing a starch-hydrolyzing enzyme with a liquid additive so as to form a liquid mixture;
(c) mixing the solid mixture and liquid mixture together; and
(d) extruding the resultant mixture from step (c) so as to induce hydrolysis of the native starch and chemical blending of the resultant enzyme-hydrolyzed starch and the biodegradable polyester to form the starch-based biodegradable film wherein the starch-hydrolyzing enzyme has an activity ranging from 15000 U to 40000 U and wherein said native starch has a weight ratio to said starch enzyme not greater than 190.

20. The method of claim 19, wherein the extruding in step (d) is conducted through a twin extruder.

* * * * *